US00PP14268P29

(12) United States Plant Patent
Pieters

(10) Patent No.: US PP14,268 P2
(45) Date of Patent: Nov. 4, 2003

(54) CHRYSANTHEMUM PLANT NAMED 'PJHAVAN'

(50) Latin Name: *Chrysanthemum X morifolium*
Varietal Denomination: Pjhavan

(76) Inventor: Luc Remi Johan Pieters,
Schierveldestraat 1A, B 8840
Oostnieuwkerke-Staden (BE)

( * ) Notice: Subject to any disclaimer, the term of this patent is extended or adjusted under 35 U.S.C. 154(b) by 0 days.

(21) Appl. No.: 10/122,736

(22) Filed: Apr. 14, 2002

(51) Int. Cl.[7] ..... A01H 5/00
(52) U.S. Cl. ..... Plt./289
(58) Field of Search ..... Plt./289, 287

*Primary Examiner*—Bruce R. Campell
*Assistant Examiner*—June Hwu
(74) *Attorney, Agent, or Firm*—C. A. Whealy

(57) ABSTRACT

A new and distinct cultivar of Chrysanthemum plant named 'Pjhavan', characterized by its rounded plant habit; freely branching habit; uniform and freely flowering habit; decorative-type inflorescences; golden yellow-colored ray florets; natural season flowering in mid-September in the Northern Hemisphere; and good garden performance.

3 Drawing Sheets

Botanical classification/cultivar designation: *Chrysanthemum×morifolium* cultivar Pjhavan.

BACKGROUND OF THE INVENTION

The present invention relates to a new and distinct cultivar of Chrysanthemum plant, botanically known as *Chrysanthemum×morifolium,* commercially known as a garden-type Chrysanthemum and hereinafter referred to by the name 'Pjhavan'.

The new cultivar is a product of a planned breeding program conducted by the Inventor in Oostnieuwkerke-Staden, Belgium. The objective of the breeding program is to create new garden-type Chrysanthemum cultivars having inflorescences with desirable inflorescence forms, attractive floret colors and good garden performance.

The new Chrysanthemum originated from a cross made in 1997, in Oostnieuwkerke-Staden, Belgium, of the Chrysanthemum cultivar Ballino, not patented, as the female, or seed, parent with an unidentified selection of Chrysanthemum, not patented, as the male, or pollen, parent. The new Chrysanthemum was discovered and selected by the Inventor as a single flowering plant within the progeny of the stated cross grown in a controlled environment in Oostnieuwkerke-Staden, Belgium.

Asexual reproduction of the new cultivar by terminal cuttings taken in a controlled environment in Oostnieuwkerke-Staden, Belgium since November, 1998, has shown that the unique features of this new Chrysanthemum are stable and reproduced true to type in successive generations.

SUMMARY OF THE INVENTION

The cultivar Pjhavan has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Pjhavan'. These characteristics in combination distinguish 'Pjhavan' as a new and distinct cultivar:

1. Rounded plant habit.
2. Freely branching habit; dense and full plants.
3. Uniform and freely flowering habit.
4. Decorative-type inflorescences.
5. Golden yellow-colored ray florets.
6. Natural season flowering in mid-September in the Northern Hemisphere.
7. Good garden performance.

Plants of the new Chrysanthemum differ from plants of the female parent, the cultivar Ballino, in the following characteristics:

1. Plants of the new Chrysanthemum are more upright as plants of the cultivar Ballino.
2. Plants of the new Chrysanthemum flower about five days later than plants of the cultivar Ballino.
3. Plants of the new Chrysanthemum have larger inflorescences than plants of the cultivar Ballino.

Plants of the new Chrysanthemum differ from plants of the male parent selection primarily in ray floret coloration.

Plants of the new Chrysanthemum can be compared to plants of the cultivar Borello, not patented. In side-by-side comparisons conducted in Oostnieuwkerke-Staden, Belgium, plants of the new Chrysanthemum differed from plants of the cultivar Borello in the following characteristics:

1. Plants of the new Chrysanthemum were more upright than plants of the cultivar Borello.
2. Plants of the new Chrysanthemum flowered about three to four weeks earlier than plants of the cultivar Borello.
3. Ray florets of plants of the new Chrysanthemum were lighter in color than ray florets of plants of the cultivar Borello.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering plant of 'Pjhavan'.

The photograph on the second sheet comprises a close-up view of typical inflorescences of the cultivar Pjhavan.

The photograph on the third sheet is a close up view of typical leaves of 'Pjhavan'.

DETAILED BOTANICAL DESCRIPTION

The aforementioned photographs and following observations and measurements describe plants grown in an outdoor nursery in Oostnieuwkerke-Staden, Belgium under natural daylength conditions and cultural practices which approximate those generally used in commercial garden-type Chrysanthemum production. Rooted young plants were planted in 19-cm containers during the summer and pinched about two weeks later. Plants flowered about four months later at the end of September; at that time, the photographs, observations and measurements were taken. During the production of the plants, day temperatures averaged about 19° C. and night temperatures averaged about 13° C. Measurements and numerical values represent averages for typical flowering plants. In the following description, color references are made to The Royal Horticultural Society Colour Chart, 1995 Edition, except where general terms of ordinary dictionary significance are used.

Botanical classification: *Chrysanthemum×morifolium* cultivar Pjhavan.

Parentage:

*Female, or seed, parent.*—*Chrysanthemum×morifolium* cultivar Ballino, not patented.

*Male, or pollen, parent.*—Unidentified selection of *Chrysanthemum×morifolium,* not patented.

Propagation:

*Type.*—Terminal tip cuttings.

*Time to initiate roots.*—Summer: About 10 days at 25° C. Winter: About 12 days at 20° C.

*Time to produce a rooted cutting.*—Summer: About 14 days at 25° C. Winter: About 21 days at 20° C.

*Root description.*—White, fine and fibrous.

*Rooting habit.*—Freely branching.

Plant description:

*Appearance.*—Perennial herbaceous decorative-type garden Chrysanthemum. Rounded plant habit; lateral branches initially upright, then outwardly spreading giving a uniformly rounded appearance to the plant. Freely branching with lateral branches forming potentially at every node; dense and full plants.

*Plant height.*—About 27 cm.

*Plant diameter.*—About 30 cm.

*Lateral branches.*—Length: About 17 cm. Diameter: About 2 mm. Texture: Pubescent. Color: 137B.

*Foliage description.*—Leaf arrangement: Alternate; single. Quantity per lateral branch: About twelve. Length: About 4 cm. Width: About 3 cm. Apex: Emarginate. Base: Acute. Margin: Palmately lobed, sinuate. Texture, upper and lower surfaces: Leathery; glabrous. Venation pattern: Pinnate. Color: Young foliage upper surface: 143B. Young foliage, lower surface: 143C. Fully expanded foliage, upper surface: 141B. Fully expanded foliage, lower surface: 141C. Venation, upper surface: 143C. Venation, lower surface: 143D. Petiole length: About 2.5 cm. Petiole diameter: About 2 mm. Petiole color, upper and lower surfaces: 143A.

Inflorescence description:

*Appearance.*—Decorative-type inflorescence form with elliptic ray florets. Inflorescences borne on terminals above foliage, arising from leaf axils. Disk and ray florets arranged acropetally on a capitulum. About ten inflorescences per lateral branch. Inflorescences persistent.

*Flowering response.*—Under natural season conditions, plants flower in mid-September in the Northern Hemisphere and continue to flower for about four weeks depending on weather conditions.

*Fragrance.*—Slight; fragrance typical of species.

*Inflorescence bud* (*stage of showing color*).—Height: About 8 mm. Diameter: About 1.2 cm. Shape: Ovoid. Phyllary color: 143A.

*Inflorescence size.*—Diameter: About 3.2 cm. Depth (height): About 1.3 cm. Disc diameter: About 1 cm.

*Ray florets.*—Shape: Elliptic. Length: About 1.3 cm. Width: About 6 mm. Apex: Rounded. Base: Obtuse. Margin: Entire. Texture: Smooth, glabrous, satiny. Number of ray florets per inflorescence: About 50. Color: When opening, upper surface: 14A. When opening, lower surface: 32A. Opened inflorescence, upper surface: 15C; fading to 14C with subsequent development. Opened inflorescence, lower surface: 28A to 28B.

*Disc florets.*—Shape: Tubular, apex dentate. Length: About 5 mm. Width: About 0.7 mm. Color: Immature: 17A. Mature: 16A.

*Peduncle.*—Angle: Erect. Length: About 3 cm. Diameter: About 1 mm. Texture: Smooth. Strength: Flexible, but strong. Color: 137B.

*Reproductive organs.*—Androecium: Present on disc florets only. Anther color: 9A. Gynoecium: Present on both ray and disc florets. No pollen has been observed to date.

*Seed/fruit.*—Seed nor fruit production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from −3 to 35° C.

It is claimed:

1. A new and distinct cultivar of Chrysanthemum plant named 'Pjhavan', as illustrated and described.

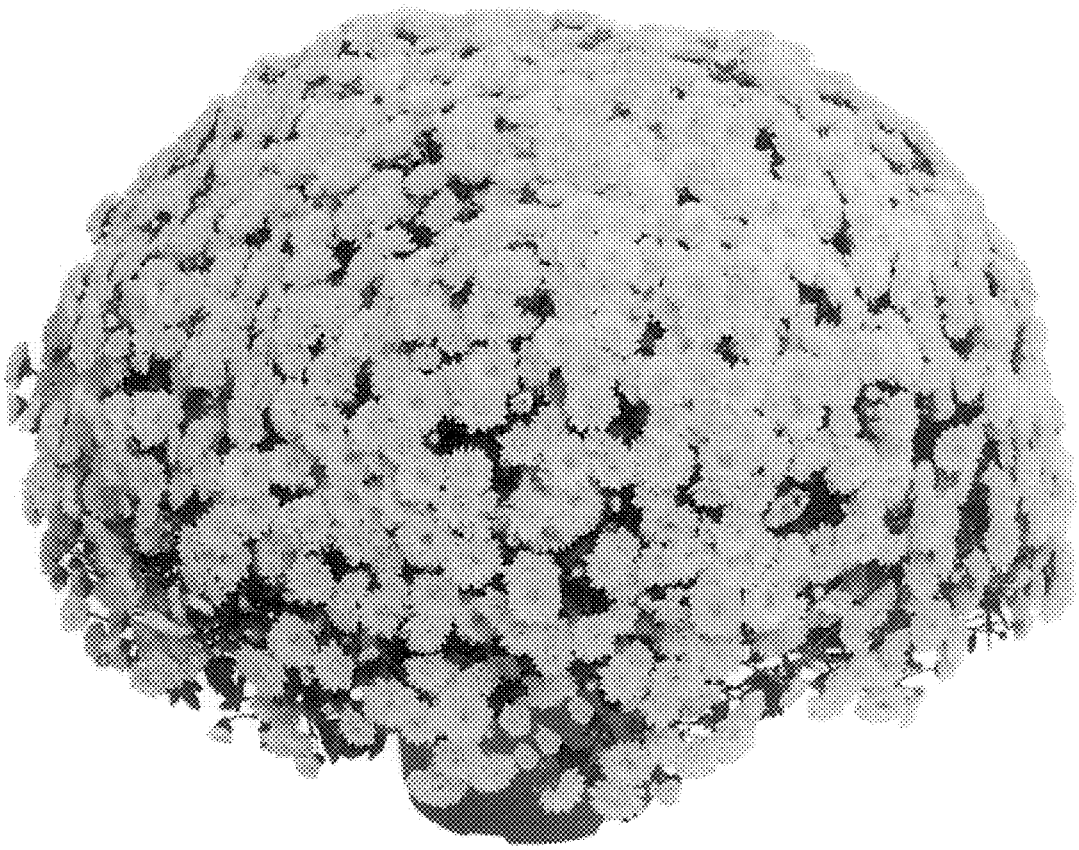

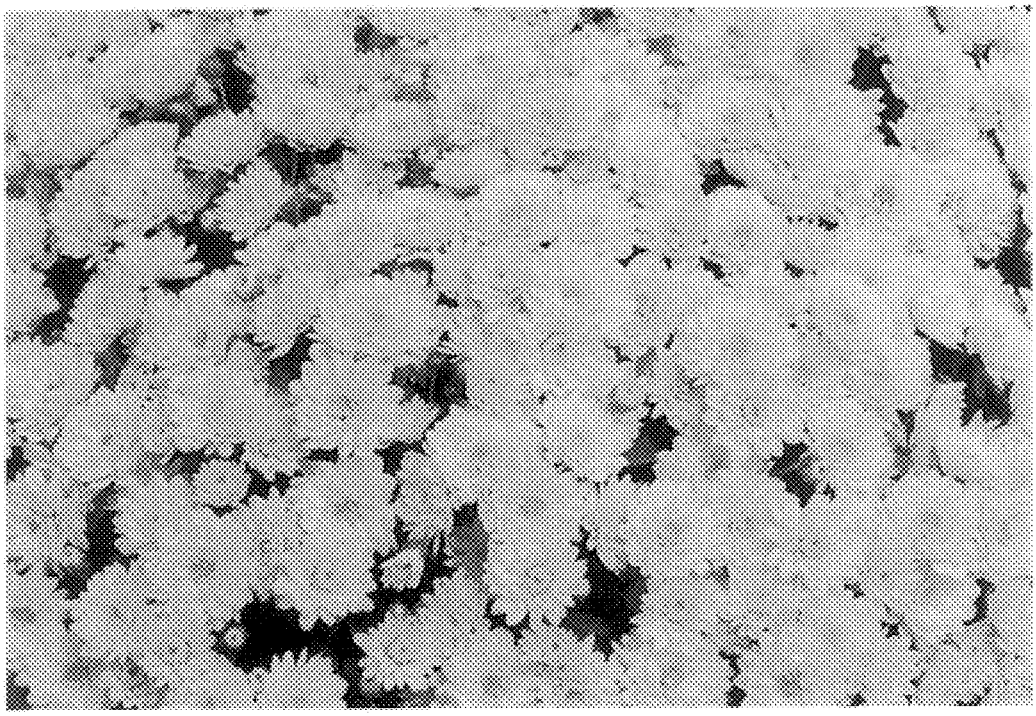

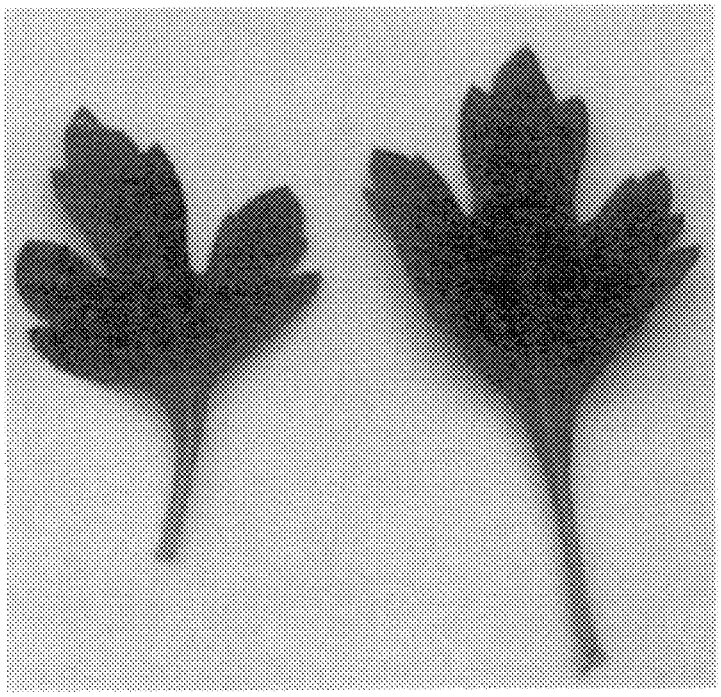

* * * * *